(12) United States Patent
Antelman

(10) Patent No.: US 6,645,531 B1
(45) Date of Patent: Nov. 11, 2003

(54) MULTIVALENT ELECTRON ACTIVE COMPOSITIONS AND METHODS OF MAKING AND USING SAME

(75) Inventor: Marvin S. Antelman, Rehovot (IL)

(73) Assignee: Marantech Holding LLC, East Province, RI (US)

( * ) Notice: Subject to any disclaimer, the term of this patent is extended or adjusted under 35 U.S.C. 154(b) by 0 days.

(21) Appl. No.: 09/692,126

(22) Filed: Oct. 20, 2000

Related U.S. Application Data

(63) Continuation-in-part of application No. 09/552,172, filed on Apr. 18, 2000, now Pat. No. 6,258,385.
(60) Provisional application No. 60/214,503, filed on Jun. 28, 2000, provisional application No. 60/184,053, filed on Feb. 22, 2000, and provisional application No. 60/174,793, filed on Jan. 6, 2000.

(51) Int. Cl.$^7$ .................... A61K 33/34; A61K 33/24; A61K 33/26; A61K 33/32
(52) U.S. Cl. .................... 424/635; 424/617; 424/630; 424/639; 424/646; 424/647; 424/648; 424/653
(58) Field of Search .................... 424/600, 617, 424/618, 630, 634, 639, 646, 647, 648, 653

(56) References Cited

U.S. PATENT DOCUMENTS

| | | | |
|---|---|---|---|
| 3,923,982 A | 12/1975 | Lamand et al. | 424/140 |
| 4,447,254 A | 5/1984 | Hughes et al. | 71/67 |
| 4,828,832 A | 5/1989 | De Cuellar et al. | 424/618 |
| 4,952,411 A | 8/1990 | Fox, Jr. et al. | 424/618 |
| 5,017,295 A | 5/1991 | Antelman | 210/764 |
| 5,073,382 A | 12/1991 | Antelman | 424/604 |
| 5,078,902 A | 1/1992 | Antelman | 210/764 |
| 5,089,275 A | 2/1992 | Antelman | 424/602 |
| 5,098,582 A | 3/1992 | Antelman | 210/759 |
| 5,211,855 A | 5/1993 | Antelman | 210/758 |
| 5,223,149 A | 6/1993 | Antelman | 210/764 |
| 5,334,588 A | 8/1994 | Fox, Jr. et al. | 514/171 |
| 5,336,416 A | 8/1994 | Antelman | 210/764 |
| 5,336,499 A | 8/1994 | Antelman | 424/405 |
| 5,571,520 A | 11/1996 | Antelman | 424/405 |
| 5,612,019 A | 3/1997 | Gordon et al. | 424/9.32 |
| 5,676,977 A | 10/1997 | Antelman | 424/618 |
| 5,772,896 A | 6/1998 | Denkewicz, Jr. et al. | 210/754 |

FOREIGN PATENT DOCUMENTS

JP 2000060976 2/2000

OTHER PUBLICATIONS

STN/CAS online, file CAPLUS, Acc. No. 1999:748588, Doc. No. 131:340719 (JP 11322408 A2 (Ohne et al.), Nov. 24, 1999), Abstract.*
STN/CAS online, file CAPLUS, Acc. No. 1997:195107, Doc. No. 126:182656 (JP 09012415 A2 (Doi et al.), Jan. 14, 1997), Abstract.*
Antelman, Marvin S.; "Silver (II,III) Disinfectants"; *Soap/Cosmetics/Chemical Specialties*, Mar. 1994, pp. 52–59.
Antelman, Marvin S.; *Abstracts of American Chemical Society*; 1992(203).
Antelman, Marvin S.; "Anti–Pathogenic Multivalent Silver Molecular Semiconductors"; *Precious Metals*; 1992(16); pp. 141–149.
Antelman, Marvin S.; "Multivalent Silver Bactericides"; *Precious Metals*; 1992(16); pp. 151–163.
Fung, Man C. and Bowen, Debra L.; "Silver Products for Medical Indications: Risk–Benefit Assessment", *Clinical Toxicology*, 1996, pp. 119–126.
Dorland et al., *Dorland's Illustrated Medical Dictionary*, Philadelphia: W.B. Saunders Company, 1994, 28$^{th}$ Edition, p. 351, 759, and 760.
Gennaro, A., Remington's Pharmaceutical Sciences, Easton, PA: Mack Publishing Company, 1985, 17$^{th}$ Edition, p. 1573–1575, 1585–1594, and 1601.

* cited by examiner

*Primary Examiner*—Jose' G. Dees
*Assistant Examiner*—Frank Choi

(57) ABSTRACT

The present invention is directed to pharmaceutical compositions that include a therapeutically effective amount of at least one electron active compound, or a pharmaceutically acceptable derivative thereof, that has at least two polyvalent cations, at least one of which has a first valence state and at least one of which has a second, different valence state. Preferred compounds include Bi(III,V) oxide, Co(II,III) oxide, Cu(I,III) oxide, Fe(II,III) oxide, Mn(II,III) oxide, and Pr(III,IV) oxide, and optionally Ag(I,III) oxide. These compounds may be in a crystalline state having metallic cations of two different valences, or electronic states, in the inorganic crystal. In addition, the invention relates to methods for prevention, management, or treatment of a condition using these compounds or pharmaceutical compositions including the same.

7 Claims, No Drawings

US 6,645,531 B1

MULTIVALENT ELECTRON ACTIVE COMPOSITIONS AND METHODS OF MAKING AND USING SAME

CROSS-REFERENCE TO RELATED APPLICATIONS

This application is a continuation-in-part of Application No. 09/552,172, filed Apr. 18, 2000, now U.S. Pat. No. 6,258,385 and claims benefit of Provisional Application No. 60/174,793, filed Jan. 6, 2000, No. 60/184,053, filed Feb. 22, 2000, and No. 60/214,503, filed Jun. 28, 2000.

FIELD OF THE INVENTION

The present invention relates to electron active compounds and compositions that have polyvalent cations in their crystal lattices. In addition, the present invention also includes a method of making such electron active compounds. The present invention also relates to methods for the prevention, treatment, or management of conditions, or symptoms thereof, by administering one or more such compounds or compositions.

BACKGROUND OF THE INVENTION

Tetrasilver tetroxide has been demonstrated to possess unique properties arising from electrostatic concepts of metal cation interaction. Such silver molecules have also been disclosed for various uses, as they are reported to be non-toxic to animals and humans. M. Antelman, "Anti-Pathogenic Multivalent Silver Molecular Semiconductors," *Precious Metals*, vol. 16:141–149 (1992); M. Antelman, "Multivalent Silver Bactericides," *Precious Metals*, vol. 16:151–163 (1992). For example, tetrasilver tetroxide activated with an oxidizing agent is disclosed for use in bactericidal, fungicidal, and algicidal use, such as in municipal and industrial water treatment applications and for the treatment of AIDS.

A variety of sources also report the use of certain divalent silver compounds for water treatment, as well as the use of such compounds, typically in combination with certain oxidizing agents, metals, or other compounds, as disinfectants, bactericides, algicides, and fungicides. One source also reports a single in vitro study of the use of such compounds for the treatment of AIDS. These sources include M. Antelman, "Silver (II, III) Disinfectants," *Soap/Cosmetics/Chemical Specialties*, pp. 52–59 (Mar., 1994), and U.S. Pat. Nos. 5,017,295; 5,073,382; 5,078,902; 5,089,275; 5,098,582; 5,211,855; 5,223,149; 5,336,416; and 5,772,896.

U.S. Patent No. 5,336,499 discloses tetrasilver tetroxide and persulfate compositions having certain in vitro antipathogenic properties, i.e., bactericidal, fungicidal, viricidal, and algicidal, in certain concentrations as low as 0.3 ppm, particularly in nutrient broth cultures. The persulfate is disclosed as being an oxidizing agent that activates the tetroxide crystals. Also disclosed are an in vitro study regarding the inhibition of yeast growth in nutrient broth and the formulation of a gynecological cream and douche based on these results, and a report of an in vitro AIDS test with the compositions indicating total suppression of the virus at 18 ppm.

U.S. Pat. No. 5,571,520 discloses the use of molecular crystals of tetrasilver tetroxide, particularly with oxidizing agents to enhance the efficiency of such devices, for killing pathogenic microorganisms, such as staph infections. Amounts of 10 ppm sodium persulfate as an oxidizing agent were used with certain amounts of silver tetroxide in the reported in vitro testing. One human study involved in vivo curing of a gynecological yeast infection with 10 ppm of the silver tetroxide and 40 ppm sodium persulfate. Other in vivo topical studies report in conclusory fashion the cure of a single case of athlete's foot with a solution of 100 ppm of the composition and the cure of a single case of toenail fungus with a 25% suspension of the composition.

U.S. Pat. No. 5,676,977 discloses intravenously injected tetrasilver tetroxide crystals used for destroying the AIDS virus, AIDS synergistic pathogens, and immunity suppressing moieties (ISM) in humans. The crystals were formulated for a single injection at about 40 ppm of human blood. This reference also discloses the compositions cause hepatomegaly, also known as enlarged liver, albeit with no reported loss of liver function.

The aforementioned references report detailed descriptions of the mechanism via which the multivalent silver molecular crystal devices were believed to operate. A discussion of such results and concepts was presented at a Seminar entitled "Incurable Diseases Update" (Weizmann Institute of Science, Rehovot, Israel, Feb. 11, 1998). The title of this presentation was "Beyond Antibiotics, Non Toxic Disinfectants and Tetrasil™ (a composition including tetrasilver tetroxide)." In this paper, it was reported that the effects of the electron transfer involved with respect to the tetroxide, rendered it a more powerful germicide than other silver entities. Other patents cover multivalent silver antimicrobial compositions, e.g., U.S. Pat. No. 5,017,295 for Ag(II) and U.S. Pat. No. 5,223,149 for Ag (III). These are stronger antimicrobial agents than Ag (I) compounds, but they pale by comparison to tetrasilver tetroxide. Likewise, colloidal silver that derives its germicidal properties from trace silver (I) ions it generates in various environments is also less effective. Accordingly, the oligodynamic properties of these entities may be summarized as follows, which is referred to as the Horsfal series:

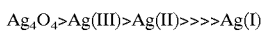

$Ag_4O_4 > Ag(III) > Ag(II) >>>> Ag(I)$

Another property of the tetrasilver tetroxide is that it does not stain organic matter such as skin in like manner as Ag(I) compounds do. In addition, it is light stable.

Further, synthetic routes for making Bi(III,V) oxide are detailed and reviewed in *Gmelins Handbuch DerAnorganischen Chemie*, vol. 16:642 (1964). Also, Co(II,III) oxide, Fe(II,III) oxide, Mn(II,III) oxide, and Pr(III,IV) oxide can all be found in nature. These five multivalent metal oxides are also all available commercially.

In view of the beneficial properties of tetrasilver tetroxide, it could be desirable to find other medicinal uses for this compound, as well as to discover other electron active metal oxides that provide similar properties.

SUMMARY OF THE INVENTION

The present invention relates to pharmaceutical compositions that include a therapeutically effective amount of at least one electron active compound, or a pharmaceutically acceptable derivative thereof, that has at least two polyvalent cations, at least one of which has a first valence state and at least one of which has a second, different valence state. Advantageously, the pharmaceutical composition may have antipathogenic efficacy. Preferably, the at least one electron active compound includes a metal oxide. In one embodiment, the metal oxide includes at least one of bismuth, cobalt, copper, iron, manganese, praseodymium, or a combination thereof. Preferably, in that embodiment, the metal oxide includes at least one of Bi(III,V) oxide, Co(II, III) oxide, Cu(I,III) oxide, Fe(II,III) oxide, Mn(II,III) oxide, Pr(III,IV) oxide, or a combination thereof. In another embodiment, the metal oxide can include Ag(I,III) oxide. Alternately, the pharmaceutical composition does not include tetrasilver tetroxide. In another alternate embodiment, the pharmaceutical composition does not include tricobalt tetroxide. In one embodiment, the pharmaceutical composition may include at least two different electron active compounds. In another embodiment, the compound may be in powder or granular form.

In a preferred embodiment, the first valence and the second valence of the at least two polyvalent cations differ by at least 1, preferably by 1 or 2. In another preferred embodiment, the first valence and the second valence of the at least two polyvalent cations differ by more than 2. Advantageously, the electron active compound has at least one polyvalent cation which has an $EMF^{ox}$ of at least about +0.1 Volts.

In one embodiment, the amount of the at least one electron active compound is present in an amount from about 1 ppm to 500,000 ppm, based on the weight of the composition. If desired, the pharmaceutical composition can include a pharmaceutically acceptable carrier. Optionally, the composition can also include an oxidizing agent, preferably present in an amount sufficient to enhance the efficacy of the active compound but insufficient to cause skin irritation. Preferably, the oxidizing agent includes a peroxy acid salt of a persulfate.

In a preferred embodiment, the at least one compound has antimicrobial efficacy, preferably of at least about 20%. In another embodiment, the antimicrobial efficacy is at least about 50%. In yet another embodiment, the antimicrobial efficacy is at least about 80%. In these embodiments, about 100 ppm of the at least one compound is placed in contact for about 10 minutes with microbes having a cell density of approximately 75,000 CFU/mL.

Also an aspect of the present invention is a pharmaceutical composition comprising tetracopper tetroxide compound. Advantageously, the tetracopper tetroxide contains two copper(I) ions, two copper(III) ions, and four oxygen atoms in a crystal lattice.

Another aspect of the present invention is a method of preventing, treating, or managing a condition of a patient which includes administering a therapeutically effective amount of at least one of the electron active compounds described herein, or a pharmaceutically acceptable derivative thereof, to prevent, treat, or manage the condition, or a symptom thereof. In one embodiment, the method excludes tetrasilver tetroxide. In a preferred embodiment, the patient is a mammal, preferably, a human. Advantageously, the electron active compound(s) can be administered topically, parenterally, or transdermally, preferably in an amount from about 5 ppm to 500,000 ppm, based on the weight of the composition. In one embodiment, at least two different electron active compounds are administered.

In another embodiment, the method can include administering one or more additional different therapeutic agents, present in an amount sufficient to facilitate the prevention, treatment, or management of the condition. In this embodiment, the one or ore additional therapeutic agents may optionally be administered concurrently with the electron active compound(s).

Another aspect of the present invention relates to a method of facilitating the killing of a pathogen which includes administering a therapeutically effective amount of at least one electron active compound, or a pharmaceutically acceptable derivative thereof, that has at least two polyvalent cations, at least one of which having a first valence state and at least one of which having a second different valence state.

The present invention also involves a method of inhibiting the growth of a pathogen which comprises administering a therapeutically effective amount of at least one electron active compound, or a pharmnaceutically acceptable derivative thereof, that has at least two polyvalent cations, at least one of which having a first valence state and at least one of which having a second different valence state.

In one embodiment, these methods exclude the administration of tetrasilver tetroxide. In either of these methods, the pathogen can include a gram-positive bacillus or coccus; a gram-negative bacillus or coccus; an acid-fast bacterium; another type of bacterium; a fungus; a parasitic microbe; a virus; or a combination thereof.

Tetracopper tetroxide, containing two copper(I) ions, two copper(III) ions, and four oxygen atoms, is one preferred electron active compound, while the administration of tetrasilver tetroxide for treating certain conditions is excluded.

In addition, the present invention relates to a process for preparing tetracopper tetroxide, which includes: combining a copper(I)-containing compound and a caustic solution to form a reactant solution; and heating the reactant solution to a temperature and for a time sufficient to produce a detectable amount of the tetracopper tetroxide compound. Advantageously, the copper(I)-containing compound includes a non-solvated inorganic copper(I) oxide, such as cuprous oxide.

The caustic solution generally contains a strong caustic base and a peroxy acid salt. Preferably, the strong caustic base includes a hydroxide salt, and the peroxy acid salt includes a persulfate.

Another aspect of the invention relates to method water with the compounds or compositions of the present invention.

DEFINITIONS

Some of the terms used in connection with the invention can be defined as follows:

The term "condition," as used herein, should be understood to refer to a traditionally identified disease, as well as a disorder, an affliction, or an ailment, particularly including those noted herein.

The terms "prevent," "preventing," and "prevention," as used herein, refer to stopping or hindering a condition, symptom, or pathogen causing a condition, in a patient who is at risk of suffering from such a condition. This also includes reducing the frequency or severity, or both, of the occurrence of such conditions or one or more symptoms thereof.

The terms "manage," "managing," and "management," as used herein, includes controlling those conditions which cannot be cured completely, reducing the time of affliction of such conditions, and the like. Preferably, the compositions prevent, treat, or manage such conditions without superficially discoloring the skin, i.e., no discoloration to the naked eye. In one embodiment, the invention relates to the treatment or management, while in another embodiment the invention relates to the prevention, of the diseases or conditions disclosed and claimed herein. The terms also include the use of the compounds or compositions of the invention to facilitate the halting, diminishing, or inhibiting of the growth or proliferation of pathogens that may accentuate, amplify, exacerbate, or cause, either directly or indirectly, a condition and/or a symptom thereof.

The term "patient" as used herein refers to animals, particularly to mammals. In one preferred embodiment, the term patient refers to humans.

The terms "adverse effects," "adverse side effects," and "side effects," as used herein, include, but are not limited to, cardiac arrhythmia, cardiac conduction disturbances, appetite stimulation, weight gain, sedation, gastrointestinal distress, headache, dry mouth, constipation, diarrhea, drug-drug interactions, superficial discoloration of the skin, dry skin, hepatomegaly, fever, fatigue, and the like. The term "cardiac arrhythmia" includes, but is not limited to, ventricular tachyrhythmia, torsades de pointes, $Q_T$ prolongation, and ventricular fibrillation.

The phrase "therapeutically effective amount" when used herein in connection with the compositions and methods of the invention, means that amount of electron active metal oxide compound(s) or composition(s), or a derivative thereof, which, alone or in combination with other drugs, provides a therapeutic benefit in the prevention, treatment, or management, of a condition. In one embodiment, the effective amount is one or more metal oxide compounds or compositions as the sole active ingredient. Different therapeutically effective amounts may be applicable for each condition, as will be readily known or determined by those of ordinary skill in the art.

The term "substantially free" means less than about 10 weight percent, preferably less than about 5 weight percent, more preferably less than about 1 weight percent, and most preferably less than about 0.1 weight percent. For example, a composition may be substantially free of added oxidizing agent or of added persulfate according to the invention.

The term "about," as used herein, should generally be understood to refer to both numbers in a range of numerals. Moreover, all numerical ranges herein should be understood to include each whole integer within the range.

The term "substantial," as used herein, means at least about 75%, preferably at least about 90%, more preferably at least about 95%, most preferably at least about 99%.

The term "valence state," as used herein, should be understood to refer to the charge on a given ion or to the charge that may be assigned to a given ion based on its electronic state.

The terms "inhibit," "inhibiting," or "inhibits," as used herein when referring to growth of an item, should be understood to refer to the act of stopping that growth, whether permanently or temporarily, or of reducing the rate of that growth, either permanently or temporarily.

DETAILED DESCRIPTION OF THE INVENTION

The tetrasilver tetroxide compounds mentioned in the background are one type of electron active compound having multivalent cations in its crystal lattice. Various additional electron active compounds have now also been identified, as well as methods for making and using the same for treating various pathogenic and non-pathogenic conditions or disorders. The electron active compounds of the present invention are believed to have unique crystal structures in that, in the case of the metal oxides, there are generally atoms of the same element in the crystal that have at least two different valences, typically at least one lower-valent metal cation and at least one higher-valent metal cation, for example, such as Co(II) and Co(III), respectively.

Exemplary electron active metal oxide compounds according to the invention include, but are not limited to, Ag(I,III), Co(II,III), Pr(III,IV), Bi(III,V), Fe(II,III), Mn(II,III), and Cu(I,III) oxides. In another embodiment, Tb(III,IV) oxide, $Tb_4O_7$, or tetraterbium heptoxide, is one electron active metal oxide compound according to the invention. As discussed below, pharmaceutical compositions including one or more of such oxide compounds are useful for treating various conditions. The composition of such exemplary electron active metal oxides is shown in tabular form below:

| e | Formula | Metal cations | Lower-valent ion | # | Higher-valent ion | # |
|---|---------|---------------|------------------|---|-------------------|---|
| 2 | $Ag_4O_4$ | Ag(I,III) | $Ag^+$ | 2 | $Ag^{+3}$ | 2 |
| 1 | $Co_3O_4$ | Co(II,III) | $Co^{+2}$ | 1 | $Co^{+3}$ | 2 |
| 2 | $Pr_6O_{11}$ | Pr(III,IV) | $Pr^{+3}$ | 2 | $Pr^{+4}$ | 4 |
| 2 | $Bi_2O_4$ | Bi(III,V) | $Bi^{+3}$ | 1 | $Bi^{+5}$ | 1 |
| 1 | $Fe_3O_4$ | Fe(II,III) | $Fe^{+2}$ | 1 | $Fe^{+3}$ | 2 |
| 1 | $Mn_3O_4$ | Mn(II,III) | $Mn^{+2}$ | 1 | $Mn^{+3}$ | 2 |
| 2 | $Cu_4O_4$ | Cu(I,III) | $Cu^+$ | 2 | $Cu^{+3}$ | 2 | e - total number of electrons believed to be exchanged;
- number of particular ion type per formula unit.

Without being bound to theory, it is believed that the electron active compounds operate against pathogens by transferring electrons between their lower-valent ions and their higher-valent ions in the crystal, thereby contributing to the death of pathogens by traversing their cell membrane surface. It would seem that this, in effect, "electrocutes" the pathogens. While these compounds have also been discovered to be suitable for use in the prevention, treatment, and management of other non-pathogenic conditions and disorders, such as autoimmune disorders, circulatory disorders, neurological disorders, and the like, the mechanism by which such conditions or disorders are prevented, treated, or managed has not yet been fully understood. In any event, the electrons in proximity to pathogens are believed to be perturbed from their balanced crystals by such labile groups as NH, $NH_2$, S—S, and SH, which can be present, for example, in a pathogen cell membrane. It is believed, however, that normal cells will not be significantly affected because they do not proliferate rapidly enough to expose these labile bonds sufficiently for the bonds to be substantially affected.

The crystals in the electron active compounds are not believed to be disturbed unless more stable complexes are formed with ligands, for example, such as those comprising a pathogen cell membrane surface in a dynamic state. Indeed, the end result of electron transfer, which is a redox reaction, results in the lower-valent metal ions being oxidized to one valence state higher and the higher-valent metal ions being reduced to one valence state lower. In one embodiment, the oxidation of the lower-valent metal ions and the reduction of the higher-valent metal ions both result in ions having the same oxidation state. Examples of such an embodiment occur when the valence difference between the metal ions in the electron active molecular crystal is 2 and such examples include, but are not limited to, Ag(I,III), Bi(III,V), and Cu(I,III) oxides. In another embodiment, the oxidation of the lower-valent metal ions and the reduction of the higher-valent metal ions result in ions having opposite oxidation states (e.g., ions with a +2 valence state are oxidized to +3, while the ions with a +3 valence state are reduced to +2). Examples of such an embodiment occur when the valence difference between the metal ions in the electron active molecular crystal is 1 and such examples include, but are not limited to, Co(II,III), Fe(II,III), Mn(II,III), and Pr(III,IV) oxides.

The metal ion of certain electron active compounds may exhibit a distinct affinity for certain elements of ligands, for example, such as sulfur, oxygen, or nitrogen, particularly when present in a pathogen's cell membrane. In many cases, the metal ion will not merely bind to these elements, but will actually form chelate complexes with their ligands. The classic example of this is Ag(I,III) oxide, the monovalent silver ion of which has an affinity for sulfur and nitrogen and the oxidized/reduced divalent ion of which forms chelate complexes with, for example, mercapto or amino groups. Thus, the electron active compound attraction for the cell membrane surfaces, for example, of pathogens, is believed to be driven by powerful electrostatic forces.

Without being bound by theory, the electron exchange may be depicted, for example, by the following series of redox half reactions:

| metal(I,III) oxides | metal(II,III) oxides | metal(III,IV) oxides | metal(III,V) oxides |
|---|---|---|---|
| $Ag^+ - e = Ag^{+2}$ | $Co^{+2} - e = Co^{+3}$ | $Pr^{+3} - e = Pr^{+4}$ | $Bi^{+3} - e = Bi^{+4}$ |
| $Ag^{+3} + e = Ag^{+2}$ | $Co^{+3} + e = Co^{+2}$ | $Pr^{+4} + e = Pr^{+3}$ | $Bi^{+5} + e = Bi^{+4}$ |
| $Cu^+ - e = Cu^{+2}$ | $Fe^{+2} - e = Fe^{+3}$ | | |
| $Cu^{+3} + e = Cu^{+2}$ | $Fe^{+3} + e = Fe^{+2}$ | | |
| | $Mn^{+2} - e = Mn^{+3}$ | | |
| | $Mn^{+3} + e = Mn^{+2}$ | | |

For each redox reaction, there is believed to be an electromotive force, which is the voltage potential of the oxidizing the higher-valent ion in the metal oxide crystal. This is denoted herein as $EMF^{OX}$. In addition to the electromotive force of oxidation, there is believed to be an associated reduction reaction involving the lower-valent ion in the metal oxide crystal. This reduction reaction may be represented simply, as tabulated above, or may represent the interaction with, for example, a ligand present on a pathogen cell membrane surface, such as one containing sulfur or nitrogen. Associated with the reduction reaction is another electromotive force, or voltage potential of the reducing the lower-valent ion. This is denoted herein as $EMF^{RE}$.

When the metal ions of the electron active metal oxide interact with, for example, a sulfur-containing ligand, the affinity of the metal ion for sulfur affects $EMF^{RE}$. The stability of a particular metal sulfide is an approximation of the affinity of a metal ion for sulfur. The following approximate association constants for sulfides indicate the trend in relative affinity of each metal ion for sulfur:

| | |
|---|---|
| Ag(I) | 49 |
| Cu(I) | 47 |
| Co(II) | 26 |
| Fe(II) | 19 |
| Mn(II) | 15 |

In general, the more stable the compound, the more negative its reduction potential in the reduction reaction, for example, in the case of elemental silver:

$$2Ag+S^{-2}-2e \rightarrow Ag_2S \quad EMF^{RE}=-0.66$$

In the case of tetrasilver tetroxide, there is a reduction reaction where Ag(I) is oxidized and an oxidation reaction where Ag(III) is reduced, as follows:

$$Ag^+ - e + S^{-2} \rightarrow AgS \quad EMF^{RE} = -0.90$$
$$Ag^{+3} + e \rightarrow Ag^{+2} \quad EMF^{OX} = +2.02$$

The voltage that is discharged from a redox reaction of the electron active metal oxides of the present invention, which voltage is denoted herein as the "electrocution voltage," is the combination of the oxidizing cation's reduction potentials and the reducing cation's reduction potential (i.e., $EMF^{OX}-EMF^{RE}$) In the case of tetrasilver tetroxide, the "electrocution voltage" is 2.92 volts. The oxidizing cation's reduction potentials, $EMF^{OX}$, of exemplary metal oxides according to the present invention are tabulated below:

| Formula | Metal cations | $EMF^{ox}$ |
|---|---|---|
| $Ag_4O_4$ | Ag(I,III) | 2.02 |
| $Co_3O_4$ | Co(II,III) | 1.81 |
| $Pr_6O_{11}$ | Pr(III,IV) | 2.86 |
| $Bi_2O_4$ | Bi(III,V) | 1.59 |
| $Fe_3O_4$ | Fe(II,III) | 0.77 |
| $Mn_3O_4$ | Mn(II,III) | 1.54 |
| $Cu_4O_4$ | Cu(I,III) | 1.80 |

As noted from the above table, praseodymium-, cobalt-, and copper-based oxides are believed to be stronger antipathogenic agents or to form better pharmaceutical compositions than manganese-, bismuth-, and iron-based oxides, and in one embodiment they are preferred for this reason. Nevertheless, in certain cases, iron exhibits stronger antipathogenic characteristics, particularly antimicrobial characteristics, compared to manganese.

Another factor, however, particularly in antipathogenic or antimicrobial efficacy, can be the sulfur/nitrogen composition, for example, of cell membranes. For example, *Staphylococcus aureus* bacteria, in a culture having a cell density of 30,000 CFU/mL, exhibit significant mortality from exposure to 100 ppm of Bi(III,V) oxide for about 10 minutes, but no significant mortality from exposure to the same concentrations of Fe(II,III) and Mn(II,III) oxides for the same contact time. This result might be explained by the far greater stability of bismuth(III) sulfide, and thus the far greater affinity of bismuth(III) for sulfur, than either of the iron(II) or manganese(II) analogs.

The electron active metal oxide compounds and compositions of the present invention may be used in any form which sufficiently retains their antipathogenic character, or other non-pathogenic ability, to prevent, treat, or manage one or more of the conditions noted herein.

These compounds or compositions may be used as antipathogenic agents, such as antimicrobial, antibacterial, antiviral, or anti-algal agents, or a combination thereof. In another embodiment, the compounds or compositions may be used for preventing, treating, and/or managing various conditions that are non-pathogenic. For example, non-pathogenic conditions are believed to include certain autoimmune disorders, neurological disorders, and circulatory disorders. While the exact mechanism of the activity of such compounds or compositions is not described herein, nonetheless, suitable prevention, treatment, and/or management of such non-pathogenic conditions may be obtained by administering the compounds or compositions of the invention as described herein and as will be readily apparent to one of ordinary skill in the art.

The compositions and methods of the invention advantageously prevent, treat, or manage dermatological diseases or conditions. The conditions against which the electron active compounds, such as metal oxides, of the present invention have utility include, but are not limited to, Madura foot, actinomycosis, oral actinomycosis, anthrax, food poisoning, botulism, wound infections, pseudomembranous colitis, colitis, gas gangrene, gangrene, tetanus, diphtheria, pharyngeal diphtheria, pleomorphic laryngeal diphtheria, cutaneous diphtheria, endocarditis, bacteremia, urinary tract infections, listerosis, meningitis, miscarriage, narcodiosis, acne, skin lesions, abscesses, toxic shock syndrome, prosthesis contamination, dental caries, plaque, gum disease, gingivitis, subacute endocarditis, bacterial pneumonia, otitis, sinusitis, cat scratch fever, septicemia, abdominal and pelvic abscesses, Oroya fever, systemic Oroya fever, verruga peruana, cutaneous verruga peruana, whooping cough, Lyme disease, epidemic relapsing fever, brucellosis, granuloma inguinale granulomatic, donovanosis, gastroenteritis, nosocomial infections, tularemia, bacterial vaginitis, urethritis, bacterial conjunctivitis, chancroid, otitis media, chronic gastritis, peptic ulcer, diarrhea, Legionnaires' disease, leptospirosis, gonorrhea, arthritis, periodontal disease, salmonellosis, typhoid fever, shigellosis, rat bite fever, pharyngitis, scarlet fever, syphilis, cholera, Asiatic cholera, Yersina arthritis, bubonic plague, chronic pulmonary disease, Hansen's disease, leprosy, tuberculosis, dermal tuberculosis, psittachosis, ornithosis, conjunctivitis, trachoma, lymphogranuloma venereum, genital tract infections, Q fever, primary atypical pneumonia, rickettsial pox, typhus, epidemic typhus, Rocky Mountain spotted fever, tsutsugamushi fever, nongonococcal urethritis, human erlichiosis, meningococcal meningitis, skin infections, corneal infections, external ear infections, candidiasis, monoiliasis, thrush, candidosis, mucositis, bacteremia, hepatitis, hepatitis A, hepatitis B, hepatitis C, hepatitis E, coccidiomycosis, lymphadenitis, balantidiasis cryptosporidosis, amoebiasis, amoebic dysentery, giardiasis, giardia enteritis, leishmaniasis, Kala-azar, malaria, toxoplasmosis, trypanosomiasis, Chagas disease, African sleeping sickness, dengue, Japanese encephalitis, Rift Valley fever, Ebola hemorrhagic fever, Venezuelan hemorrhagic fever, hantavirus pulmonary syndrome, hemorrhagic fever with renal syndrome, cytomegalovirus infection, poliomyelitis, West Nile virus disease, influenza, measles, condyloma, encephalitis, ankylosing spondylitis, arteritis, inflammatory bowel disease, polyarteritis nodosa, rheumatic fever, systemic Lupus erythematosus, Alzheimer's disease, multiple sclerosis, osteoporosis, Crohn's disease, strep throat, yellow fever, eczema, psoriasis, dernatitis, disease-induced skin ulcers, undefined tropical diseases, shingles, rashes, heat rashes, bedsores, cold sores, blisters, boils, herpes simplex, acne, pimples, skin chafing, skin cracking, itchiness, skin peeling, warts, one or more symptoms thereof, or any combination thereof. In another embodiment, the condition includes HIV (AIDS), or one or more symptoms. It should be understood that the invention includes the use of the compounds or compositions to prevent, treat, or manage each of these conditions individually or multiple conditions concurrently or sequentially. Thus, the prevention, treatment, or management of each condition should be understood as a separate embodiment.

The pathogens which may be killed by, or the growth or proliferation of which may be halted, diminished, or inhibited by, the electron active metal oxides of the present invention include, but are not limited to, gram-positive bacilli and cocci; gram-negative bacilli and cocci; acid-fast bacteria; other bacteria; fungi; parasitic microbes, e.g., protozoa; and viruses.

Examples of gram-positive bacilli and cocci include, but are not limited to, Actinomedurae, *Actinomyces israelii, Bacillus anthracis, Bacillus cereus, Clostridium botulinum, Clostridium difficile, Clostridium perfringens, Clostridium tetani*, Corynebacterium, *Enterococcusfaecalis, Listeria monocytogenes*, Nocardia, *Propionibacterium acnes, Staphylococcus aureus, Staphylococcus epiderm, Streptococcus mutans, Streptococcus pneumoniae*, and combinations thereof.

Examples of gram-negative bacilli and cocci include, but are not limited to, *Afipia felis*, Bacteriodes, *Bartonella bacilliformis, Bortadella pertussis, Borrelia burgdorferi, Borrelia recurrentis*, Brucella, *Calymmatobacterium granulomatis*, Campylobacter, *Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis*, and combinations thereof.

Examples of acid-fast bacteria include, but are not limited to, *Myobacterium avium, Myobacterium leprae, Myobacterium tuberculosis*, and combinations thereof.

Examples of other bacteria not falling into the other three categories include, but are not limited to, *Bartonella henseiae, Chlamydia psittaci, Chlamydia trachomatis, Coxiella bumetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcusfaecium*, Meningococci, and combinations thereof.

Examples of fungi include, but are not limited to, Aspergilli, Candidae, *Candida albicans, Coccidioides immitis*, Cryptococci, and combinations thereof.

Examples of parasitic microbes include, but are not limited to, *Balantidium coli, Cryptosporidium parvum, Cyclospora cayatanensis*, Encephalitozoa, *Entamoeba histolytica, Enterocytozoon bieneusi, Giardia lamblia*, Leishmaniae, Plasmodii, *Toxoplasma gondii*, Trypanosomae, *trapezoidal amoeba*, and combinations thereof.

Examples of viruses include, but are not limited to, Arboviruses, Ebola virus, Guanarito virus, Hanta virus, Hantaan virus, Hepatitis A, Hepatitis B, Hepatitis C, Hepatitis E, other Hepatitis viruses, Herpes-type viruses, Poliovirus, West Nile virus, Echo virus, and combinations thereof.

The antipathogenic or non-pathogenic compositions of the present invention may optionally further include the use of one or more additional therapeutic agents known to treat a condition, or a symptom thereof. Examples of such additional therapeutic agents include, but are not limited to, chelating agents, vitamins, minerals, silica hydride microclusters, analgesics, Sambucol™, aspirin, and the like.

The electron active metal oxide compounds of the present invention may also be used for water treatment, for example, as disclosed in U.S. Pat. No. 5,223,149 and 5,336,416. Optionally but preferably, the electron active metal oxides used for treating a body of water are any listed above, more preferably provided that the metal oxide does not include tetrasilver tetroxide. It is also more preferable, in the previous embodiment, that the metal oxide does not include tetracopper tetroxide.

The administration of one or more active ingredients and/or optional therapeutic agent(s), in accordance with the methods of the invention may occur together, concurrently but separately, sequentially, or a combination thereof. The optional additional therapeutic agent is generally a compound other than an electron active metal oxide compound.

The antipathogenic or antimicrobial performance of certain metal oxides may be improved or enhanced by the presence of an oxidizing agent. This is particularly the case when the metal oxide compounds or compositions are present in low amounts, i.e., typically less than 45 ppm, and more commonly when present in an amount less than about 40 ppm, based on the weight of the composition. In such situations, an oxidizing agent may be included in certain compositions of the invention in small amounts when the compositions are administered by certain routes. In such an embodiment, the oxidizing agent includes a peroxy acid salt, preferably a Group I salt of a persulfate, more preferably potassium persulfate. In another embodiment, the oxidizing agent includes the same peroxy acid salt which was present as a starting material in the reaction to form the particular electron active metal oxide. The oxidizing agent may advantageously be present in the composition in amounts from about 1 ppm to 500 ppm, based on the weight of the composition. In alternate embodiments, there may be from about 5 ppm to 200 ppm or from about 10 ppm to 100 ppm of oxidizing agent, based on the weight of the composition.

It is believed that the additional presence of certain types or amounts of oxidizing agent(s) may tend to irritate the skin, particularly when the compound or composition including metal oxide(s) is present in large amounts, such as greater than 50 ppm, based on the weight of the composition. In one embodiment, as more compound or composition is administered, a correspondingly smaller amount of undesirable oxidizing agent is required. Thus, in some embodiments, it has been found that the additional oxidizing agent is unnecessary and in fact undesirable for the purpose of treating certain conditions described herein, since the additional oxide may have or contribute to an undesirable side effect, for example, such as skin irritation when applied topically. For those embodiments, the compositions minimize the amount of additional oxidizing agent, such as persulfate, or are substantially or completely free of added persulfates or other oxidizing agents.

Certain of the electron active metal oxides may be black in color, such that care must be taken when formulating suitable topical pharmaceutical compositions according to the invention to inhibit blackening or superficial discoloration of the skin. Without being bound by theory, it is believed that larger amounts of such compositions promote increased superficial discoloration. Thus, in one embodiment, the pharmaceutical compositions preferably have an insufficient amount of metal oxide composition to cause visible skin discoloration.

Additionally, it was found by rigorous testing that certain silver tetroxide-containing compositions were comparatively non-toxic compared to silver salts, such as conventional formulations of silver nitrate, silver sulfadiazine, and benzoyl peroxide. Since these silver tetroxide compositions were effective at certain ppm concentrations in killing pathogens in nutrient broth and for water treatment, commercial concentrates were formulated with 2% of the tetrasilver tetroxide. For acceptance of the oxide in commerce, for which EPA registration No. 3432-64 was obtained, it was necessary for the $Ag_4O_4$ to undergo a series of toxicity tests. A 3% concentrate was used and evaluated by a certified laboratory employing good laboratory practice (GLP) according to the Code of Federal Regulations for this purpose. The results were as follows:

| | |
|---|---|
| Acute Oral Toxicity | $LD_{50}$ Greater than 5,000 mg/Kg |
| Acute Dermal Toxicity | $LD_{50}$ Greater than 2,000 mg/Kg |
| Primary Eye Irritation | Mildly irritating |
| Primary Skin Irritation | No irritation |
| Skin Sensitization | Non-Sensitizing |

Subsequent evaluations conducted according to the invention showed that unless persons were prone to silver allergies, the pure tetrasilver tetroxide compositions according to the invention could be applied to the skin without any ill effects or evidence of irritation, despite the fact that the compositions of the invention can be a powerful oxidizing agent. This can perhaps be explained by the stability manifested by the $K_A$ of the tetrasilver tetroxide compositions, which is approximately $7.9 \times 10^{-13}$.

Where the electron active compositions according to the invention are applied to the skin, they may be combined with a carrier in an amount from about 5 ppm to 500,000 ppm, more preferably from about 50 ppm to 250,000 ppm of the electron active metal oxide composition, based on the weight of the composition. In various embodiments, the compositions are provided in amounts from about 400 ppm to 100,000 ppm, from about 1,000 ppm to 70,000 ppm, from about 10,000 ppm to 50,000 ppm, or from about 20,000 ppm to 40,000 ppm, based on the weight of the composition. In one preferred embodiment, the compositions are formulated with about 25,000 ppm to 35,000 ppm of metal oxide, based on the weight of the composition. It will be readily understood by those of ordinary skill in the art that the ppm concentration of electron active compound(s), such as metal oxide, in the composition is based on the total weight of the composition.

When prevent, treating, or managing conditions, a preferred embodiment employs amounts of about 0.1 to 10 percent by weight, about 0.25 to 5 percent by weight, or about 2 to 4 percent by weight of the compounds or compositions of the invention. The compositions, when applied topically, can be applied to the skin about1 to 3 times per day until the condition is suitably cured or satisfactorily controlled. In one embodiment, the composition may generally be topically applied at a dosage level of from about 1 mg to 1000 mg per $cm^2$ of skin surface, preferably about 10 mg to 500 mg per $cm^2$ of skin surface. When applied topically, a preferred carrier includes petroleum jelly, such as white petroleum jelly. For example, a suitable white petroleum jelly is available from Penreco of Houston, Tex.

Most of the metal oxide compounds for use according to the invention are commercially available from various sources. Tetrasilver tetroxide compositions for use according to the invention have been commercially sold under the poorly named "Ag(II) OXIDE" tradename. They may be obtained from Aldrich Chemical Co., Inc., having a place of business in Milwaukee, Wis. The chemical synthesis of tetrasilver tetroxide compounds can be performed according to the method described on page 148 in M. Antelman, "Anti-Pathogenic Multivalent Silver Molecular Semiconductors," *Precious Metals*, vol. 16:141–149 (1992) by reacting silver nitrate with potassium peroxydisulfate according to the following equation in alkali solutions:

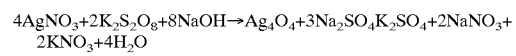

To the extent necessary to understand the present invention, the disclosure of Antelman is hereby incorporated herein by express reference thereto.

Tetracopper tetroxide, also referred to herein as Cu(I,III) oxide or $Cu_4O_4$, is a preferred electron active compound in accordance with the invention. This compound may be prepared as follows.

Suitable copper-based starting materials for this reaction include at least one copper(I)-containing material. In one embodiment, a water soluble copper(I) salt can be used. Typically, a water soluble copper(I) salt can be prepared by dissolving an inorganic copper(I) compound, for example, such as cuprous oxide, in an appropriate acid, for example, an organic acid, such as acetic acid. Since soluble copper(I) salts are not readily commercially available at the present time, however, a non-solvated inorganic copper(I) compound, such as cuprous oxide itself, can be used as the copper(I)-containing starting material. In addition, other copper(I)-containing materials, either inorganic, such as a copper(I) oxide, or organic, such as an organometallic copper(I) compound, or both, may be used, where the copper(I)-containing material(s) are sufficiently soluble in an aqueous or organic solution to allow reaction with other materials to form an electron active copper oxide compound.

The copper(I)-containing starting material is combined with an aqueous caustic solution. This caustic solution preferably contains two components: a strong caustic base and a peroxy acid salt. Examples of suitable strong caustic bases include Group I and Group II hydroxides, preferably sodium hydroxide or potassium hydroxide. Examples of suitable peroxy acid salts include Group I salts of persulfates, preferably potassium persulfate.

The copper-based starting material is typically the limiting reagent in such a preparation. The ratio of each of the components in the caustic solution to that of the copper-based starting material is theoretically set by the stoichiometry of the particular reaction. In one preferred embodiment, there is a relative molar excess, i.e., an amount more than stoichiometrically necessary, of each of the components in the caustic solution with respect to the copper-based starting material. When a strong caustic base and a peroxy acid salt are present in the caustic solution, the relative molar excesses of the components may be at least about 50% and at least about 10%, respectively, preferably at least about 100% and at least about 20%, respectively, more preferably, at least about 250% and at least about 40%, respectively, most preferably at least about 500% and at least about 75%, respectively.

Generally, the reactants may be added together in any manner that comports with typical laboratory procedure. In one embodiment, the copper(I)-containing starting material is placed in a reactor, to which the strong caustic base and the peroxy acid salt are added, each typically in their own solutions. The solution containing the reactants is then typically heated to a temperature sufficient to activate a reaction, preferably sufficient to activate a reaction with no major undesirable side reactions or other undesirable effects, more preferably above about 80° C., most preferably about 90° C. to 95° C. The solution is heated for a time sufficient to facilitate the reaction, preferably to provide substantial completion of the reaction, preferably for at least about 5 minutes, more preferably for at least about 15 minutes, after which time the solution is allowed to cool or is cooled, preferably to below about 45° C., more preferably to about room temperature.

The color change of the solution, from its original color, red, to a color indicating a reaction has occurred, in this case black, may occur at the heated temperature or during or after cooling.

The purification and isolation of the desired product can be accomplished by any suitable method available to those of ordinary skill in the art. In the majority of situations, the desired reaction product is primarily a solid, but may be dissolved or dispersed in at least part of the solution. In one preferred embodiment, the solution is carefully decanted off, and then the remaining product is washed multiple times with distilled water, before being sufficiently dried. In another preferred embodiment, the solution is vacuum filtered to remove the filtrate, and the remaining product is sufficiently dried.

The yield of solid tetracopper tetroxide material, based on the reactants, is typically at least about 10%, preferably at least about 45%, more preferably at least about 75%, most preferably at least about 80%.

In addition, Fe(II,III) oxide and Mn(II,III) oxide are commercially available from Aldrich Company of Milwaukee, Wis., and Co(II,III) oxide and Pr(III,IV) oxide are commercially available from Noah Technologies of San Antonio, Tex. Also, Bi(III,V) oxide synthetic routes are detailed and reviewed in *Gmelins Handbuch Der Anorganischen Chemie*, vol. 16:642 (1964), and the oxide is available commercially from City Chemicals of New York, N.Y.

The magnitude of a prophylactic or therapeutic dose of electron active composition(s), or a derivative thereof, in the acute or chronic management of diseases and disorders described herein will vary with the severity of the condition to be prevented, treated, or managed and the route of administration. For example, oral, mucosal (including rectal and vaginal), parenteral (including subcutaneous, intramuscular, bolus injection, and intravenous, such as by infusion), sublingual, transdermal, nasal, buccal, and like may be employed. In one embodiment, a patient may gargle using the composition of the present invention. Dosage forms include tablets, troches, lozenges, dispersions, suspensions, suppositories, solutions, capsules, soft elastic gelatin capsules, patches, and the like. The dose, and perhaps the dose frequency, will also vary according to the age, body weight, and response of the individual patient. Suitable dosing regimens can be readily selected by those of ordinary skill in the art with due consideration of such factors. In general, the total daily dosage for the conditions described herein, is from about 0.1 mg to 1,000 mg of the active ingredient, i.e., one of the metal oxides described herein, or a derivative thereof. In another embodiment, the daily dosage can be from about 1 mg to 500 mg, while in another embodiment, the daily dosage can be from about 2 mg to 200 mg of the metal oxide composition. A unit dosage can include, for example, 30 mg, 60 mg, 90 mg, 120 mg, or 300 mg of metal oxide composition. Preferably, the active ingredient is administered in single or divided doses from one to four times a day, such as by topical administration. In another embodiment, the compositions are administered by an oral route of administration. The oral dosage forms may be conveniently presented in unit dosage forms and prepared by any methods available to those of ordinary skill in the art of pharmacy.

In managing the patient, the therapy may be initiated at a lower dose, e.g., from about 1 mg, and increased up to the recommended daily dose or higher depending on the patient's global response. It is further recommended that children, patients over 65 years, and those with impaired renal or hepatic function, initially receive low doses when administered systemically, and that they be titrated based on individual response(s) and blood level(s). It may be necessary to use dosages outside these ranges in some cases, as will be apparent to those of ordinary skill in the art. Furthermore, it is noted that the clinician or treating physician will know how and when to interrupt, adjust, or terminate therapy in conjunction with individual patient response.

Any suitable route of administration may be employed for providing the patient with an effective dosage of electron active metal oxide, or a derivative thereof. The most suitable route in any given case will depend on the nature and severity of the condition being prevented, treated, or managed.

In practical use, the metal oxide, or a derivative thereof, can be combined as the active ingredient in intimate admixture with a pharmaceutical carrier according to conventional pharmaceutical compounding techniques. The carrier may take a wide variety of forms and may include a number of components depending on the form of preparation desired for administration. The compositions of the present invention may include, but are not limited to, suspensions, solutions and elixirs; aerosols; or carriers, including, but not limited to, starches, sugars, microcrystalline cellulose, diluents, granulating agents, lubricants, binders, disintegrating agents, and the like.

Suitable forms in which the electron active compounds or compositions of the present invention may be used include, but are not limited to, powder, granule, flake, solution, suspension, emulsion, slurry, aerosol spray, gel, paste, and combinations thereof. In one preferred embodiment, the form is a powder or solution. When the electron active compounds are in the form of a solution, the solution may be aqueous, non-aqueous, or a combination thereof, preferably at least partially aqueous, more preferably substantially aqueous. In a preferred embodiment, the metal oxides are in an aqueous solution.

The compositions of the invention may be applied topically, e.g., either directly as a powder or in non-sprayable or sprayable form. Non-sprayable forms can be semi-solid or solid forms including a carrier indigenous to topical application and preferably having a dynamic viscosity greater than that of water. Suitable formulations include, but are not limited to, suspensions, emulsions, creams, ointments, powders, liniments, salves and the like. If desired, these may be sterilized or mixed with any available auxiliary agents, carriers, or excipients, e.g., thixotropes, stabilizers, wetting agents, and the like. One or more thixotropic agents can be included in types and amounts sufficient to increase adhesion of topically applied compositions of the invention to the skin, so as to inhibit or prevent runoff or other loss of the composition from the treatment zone on the skin. Preferred vehicles for non-sprayable topical preparations include ointment bases, e.g., polyethylene glycol-1000 (PEG-1000); conventional ophthalmic vehicles; creams; and gels, as well as petroleum jelly and the like. In one more preferred embodiment, the carrier includes a petroleum jelly. In another preferred embodiment, the carrier is formulated as a cream, gel, or lotion. In another preferred embodiment, the carrier is 3 weight percent active ingredient, 36 weight percent heavy mineral oil, 47 weight percent petroleum jelly, and 14 weight percent Tivawax P, which is available from Tivian Laboratories, Inc., of Providence, R.I. In yet another preferred embodiment, the composition may be a dry powder, such as with 5 weight percent active ingredient and 95 weight percent bismuth subgallate. These topical preparations may also contain emollients, perfumes, and/or pigments to enhance their acceptability for various usages.

The compositions may also be formulated for parenteral administration by injection (subcutaneous, bolus injection, intramuscular, or intravenous, such as by infusion), and may be dispensed in a unit dosage form, such as a multidose container or an ampule. Compositions of the electron active metal oxide, or a derivative thereof, for parenteral administration may be in the form of suspensions, solutions, emulsions, or the like, in aqueous or oily vehicles, and in addition to the active ingredient may contain one or more formulary agents, such as dispersing agents, suspending agents, stabilizing agents, preservatives, and the like.

In the case where an intravenous injection or infusion composition is employed, a suitable dosage range can be, e.g., from about 0.5 mg (0.1 ppm) to about 1,000 mg (200 ppm) total dose, preferably from about 5 mg (1 ppm) to 400 mg (80 ppm). In one preferred embodiment, the total dose can be from about 50 mg (10 ppm) to 200 mg (40 ppm). It should be understood that any suitable amount of the composition according to the invention may be administered if effective to prevent, treat, or manage one or more conditions described herein.

Pharmaceutical compositions of the present invention may be orally administered in discrete pharmaceutical unit dosage forms, such as capsules, cachets, soft elastic gelatin capsules, tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the pharmaceutically acceptable carrier which constitutes one or more necessary ingredients. In general, the compositions are prepared by uniformly and intimately admixing the active ingredient with liquid carriers or finely divided solid carriers or both, and then, if necessary, shaping the product into the desired presentation. Suitable types of oral administration include oral solid preparations, such as capsules or tablets, or oral liquid preparations. If desired, tablets may be coated by standard aqueous or nonaqueous techniques.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, granulating agent, surface active agent, dispersing agent, or the like. Molded tablets may be made by molding, in a suitable machine, a mixture of the powdered compound moistened with an inert liquid diluent. In one embodiment, each tablet, capsule, cachet, or gel cap contains from about 0.5 mg to about 500 mg of the active ingredient, while in another embodiment, each tablet contains from about1 mg to about 250 mg of the active ingredient. The amount of active ingredient found in the composition, however, may vary depending on the amount of active ingredient to be administered to the patient.

Another suitable route of administration is transdermal delivery, for example, via an abdominal skin patch.

The metal oxide(s), or a derivative thereof, may be formulated as a pharmaceutical composition in a soft elastic gelatin capsule unit dosage form by using conventional methods well known in the art, such as in Ebert, *Pharm. Tech*, 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain an additional preservative, such as methyl- and propylparabens and sorbic acid, to prevent the growth of fungi, although this is not necessary since the compounds and compositions of the invention provide anti-fungal efficacy.

Thus, in one embodiment, the invention includes a compositions formulated as a gelatin shell with an electron active metal oxide compound of the present invention, completely free of added preservatives. The active ingredient may be dissolved or suspended in a liquid vehicle or carrier, such as vegetable or mineral oils, glycols such as polyethylene glycol and propylene glycol, triglycerides, surfactants such as polysorbates, or a combination thereof.

In addition to the common dosage forms set out above, the compounds of the present invention may also be administered by controlled release means, delivery devices, or both, as are well known to those of ordinary skill in the art, such as those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are hereby incorporated herein by express reference thereto. These pharmaceutical compositions can be used to provide slow or controlled-release of the active ingredient therein using, for example, hydropropylmethyl cellulose in varying proportions to provide the desired release profile, other polymer matrices, gels, permeable membranes, osmotic systems, multilayer coatings, microparticles, liposomes, microspheres, or the like, or a combination thereof. Suitable controlled-release formulations available to those of ordinary skill in the art, including those described herein, may be readily selected for use with the tetrasilver tetroxide compositions of the invention. Thus, single unit dosage forms suitable for topical or oral administration, such as gels, lotions, cremes, tablets, capsules, gelcaps, caplets, and the like, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of the active ingredient being employed to cure or control the condition in a minimum amount of time. Advantages of controlled-release formulations may include: 1) extended activity of the active ingredient; 2) reduced dosage frequency; and 3) increased patient compliance.

Most controlled-release formulations are designed to initially release an amount of active ingredient that promptly produces the desired therapeutic effect, and gradual and continual release of other amounts of active ingredient to maintain this level of therapeutic effect over an extended period of time. In order to maintain this constant level of active ingredient in the body, the active ingredient should be released from the dosage form at a rate that will replace the amount of active ingredient being metabolized and excreted from the body.

The controlled-release of the active ingredient may be stimulated by various inducers, for example pH, temperature, enzymes, water, or other physiological conditions or compounds. The term "controlled-release component" in the context of the present invention is defined herein as a compound or compounds, including polymers, polymer matrices, gels, permeable membranes, liposomes, microspheres, or the like, or a combination thereof, that facilitates the controlled-release of the active ingredient (e.g., tetrasilver tetroxide) in the pharmaceutical composition.

The pharmaceutical compositions for use in the present invention include electron active metal oxides, or a derivative thereof, as the active ingredient, and may also contain a pharmaceutically acceptable carrier, and optionally, other therapeutic ingredients. Suitable derivatives include any available "pharmaceutically acceptable salts," which refer to a salt prepared from pharmaceutically acceptable non-toxic acids including inorganic acids, organic acids, solvates, hydrates, or clathrates thereof. Examples of such inorganic acids are nitric, sulfuric, lactic, glycolic, salicylic, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Particularly preferred acids are lactic, glycolic, and salicylic acids. The pharmaceutically acceptable salts preferably do not include halide-containing salts when tetrasilver tetroxide is present, as these salts are believed to facilitate breakdown of the oxide lattice present in the silver oxide compositions of the invention.

EXAMPLES

These and other aspects of the present invention may be more fully understood with reference to the following non-limiting examples, which are merely illustrative of the preferred embodiments of the present invention, and are not to be construed as limiting the invention, the scope of which is defined by the appended claims.

EXAMPLES 1–16

Antipathogenic Efficacy of Compositions

EXAMPLES 1–2

In Vitro Treatment of Salmonella with Compositions of Invention

A culture of Salmonella of cell density 500,000 CFU/mL was contacted for 10 minutes with approximately 4 ppm hexapraseodymium undecoxide ($Pr_6O_{11}$), which is believed to contain two distinct oxidation states of praseodymium, Pr(III) and Pr(IV), in its crystal lattice, at a pH of about 9, followed with a culture adjusted to a pH of about 10. The percentages of bacterial colonies killed by this treatment were 96.4% and 93.8%, respectively. The experiment was repeated with the same cell density of Salmonella using about 5 ppm of tricobalt tetroxide ($Co_3O_4$), which is believed to contain two distinct oxidation states of cobalt, Co(II) and Co(III), in its crystal lattice, at a pH of about 10. The percentage of bacterial colonies killed by this treatment was 92.8% after 10 minutes of contact with the oxide-containing composition.

EXAMPLES 3–4

Antipathozenic Effect of Compositions in Water Purification

The praseodymium oxide crystals of Example 1 were tested against the standard AOAC coliform culture used in water purification studies and having a 375,000 CFU/mL density. The results of this study are tabulated below:

| ppm Pr$_6$O$_{11}$ | Contact time (mins.) | pH | Bacteria mortality (%) |
|---|---|---|---|
| 4 | 5 | 7 | 68 |
| 4 | 10 | 7 | 71 |
| 10 | 5 | 7 | 65 |
| 10 | 10 | 7 | 76 |
| 5 | 5 | 9 | 84 |
| 10 | 10 | 9 | 88 |

The experiment of Example 3 was repeated with about 4 ppm of tricobalt tetroxide (Co$_3$O$_4$) according to Example 2, at a contact time of about 5 minutes at a pH of about 7. The percentage of bacterial colonies killed by this treatment was 75%.

EXAMPLE 5

In vitro Treatment of *Stayhylococcus aureus* with Compositions 1 gram of Pr (III,IV) oxide (Pr$_6$O$_{11}$) was dissolved in 20 mL of 85% phosphoric acid, which underwent substantially no redox reaction with the praseodymium oxide, such that an active solution was formed. The solution was subsequently diluted to yield a 100 ppm solution, based on the oxide component. The Pr (III,IV) oxide solution, when put in contact with Staphylococcus aureus at 220,000 CFU/mL cell density, served to kill substantially all the bacteria (100% mortality) after 10 minutes of contact with the oxide-containing composition.

EXAMPLES 6–9

In vitro Treatment of *E. coli* with Compositions of the Invention

A culture of *E. coli* bacteria having a cell density of 420,000 CFU/mL was contacted for about 10 minutes with about 6 ppm of Co (II,III) oxide, Co$_3$O$_4$, at a pH of about 7, also in the presence of 10 ppm potassium monopersulfate, which is commercially available under the trademark OXONE from DuPont De Nemours, Inc., of Wilmington, Del. The percentage of bacteria killed by this contact was 47.6%. When repeating the previous experiment using a culture having a cell density of 380,000 CFU/mL and with about 5 ppm of Pr (III,IV) oxide in the presence of about 50 ppm OXONE™, the percentage of bacteria killed was 39.5%.

A culture of *E. coli* bacteria having a cell density of 160,000 CFU/mL was contacted for about 10 minutes with about 100 ppm of Cu (1,111) oxide, Cu$_4$O$_4$. The percentage of bacteria killed by this contact was 63.8%. When repeating the previous experiment using only about half the Cu (I,III) oxide concentration, i.e., about 50 ppm, in the presence of about 200 ppm OXONE™, the percentage of bacteria killed was 97.8%.

EXAMPLES 10–13

In vitro Treatment of *E. coli* with Compositions of the Invention

Cultures of *E. coli* bacteria, each having a cell density around 100,000 CFU/mL, were each contacted for about 10 minutes with various electron active molecular metal oxide crystals according to the invention, resulting in the following percentages of bacteria killed:

| Composition of the Invention | % Bacteria Killed |
|---|---|
| Bi (III,V) oxide, Bi$_2$O$_4$ | 38% |
| Fe (II,III) oxide, Fe$_3$O$_4$ | 32% |
| Mn (II,III) oxide, Mn$_3$O$_4$ | 28% |

These experiments were repeated using reduced triiron tetroxide, Fe$_3$O$_4$, concentrations and *E. coli* cultures, each having a reduced cell density of 75,000 CFU/mL, with variable OXONE™ concentrations. When Fe (II, III) oxide was used in about 50 ppm concentration in the presence of about 200 ppm OXONE™, the percentage of bacteria killed was about 73.3%. When Fe (II,III) oxide was used in about 20 ppm concentration, in the presence of about 100 ppm OXONE™, the percentage of bacteria killed was about 49.3%.

EXAMPLES 14–16

In vitro Treatment of *Staphylococcus aureus* Using Compositions

Compositions containing about 100 ppm of Bi (III,V) oxide, Bi$_2$O$_4$, Fe (II,III) oxide, Fe$_3$O$_4$, or Mn (II,III) oxide, Mn$_3$O$_4$, were tested for antimicrobial efficacy by contacting cultures of *Staphylococcus aureus* bacteria having cell densities of 75,000 CFU/mL for about 10 minutes. The iron and manganese oxide compositions were observed to kill substantially no bacteria, whereas the composition containing dibismuth tetroxide was observed to kill about 37.3% of the bacteria.

EXAMPLE 17

Preparation of Tetracopper Tetroxide 2.4 grams each of sodium hydroxide and potassium persulfate were dissolved, each in 25 mL of distilled water, each in its own 50 mL beaker. These solutions were mixed together in another beaker, to which 700 mg of red cuprous oxide was added. This beaker was heated to approximately 90° C. and was maintained from about 90° C. and 95° C. for about 15 minutes before being allowed to cool to room temperature. The heating of the solution caused a color change from red to black, indicating a reaction of the oxide.

The solid product was purified and isolated by one of two methods: a) decanting off the solution, washing the remaining product at least seven times with distilled water, and drying the product; or b) vacuum filtering the solution and drying the product. The experimental yield was similar using either isolation method.

The average theoretical yield of Cu(I,III) oxide, or Cu$_4$O$_4$, was 83%, based on the following equation:

$$4NaOH + 2Cu_2O + 2K_2S_2O_8 \rightarrow Cu_4O_4 + 2Na_2SO_4 + 2K_2SO_4 2H_2O$$

Based on all of the test data described above, the healing mechanism associated with the use of the metal oxides of the invention to treat and manage at least some skin diseases, without being bound by theory, appears to involve mechanisms other than merely inhibiting or killing pathogens and curing infections that tend to aggravate disease and retard the natural healing process. The data indicate that healing is brought about even in cases where no abnormal bacteria counts or infection is evident. This suggests that the electron active compound(s) may also act against auto-antibodies that trigger autoimmune reactions associated with diseased tissue, as well as against other non-pathogenic conditions or diseases, such as circulatory or neurological conditions or diseases.

Although preferred embodiments of the invention have been described in the foregoing Detailed Description, it will be understood that the invention is not limited to the embodiments disclosed, but is capable of numerous rearrangements and modifications of parts and elements without departing from the spirit of the invention. It will be understood that the chemical and pharmaceutical details of every design may be slightly different or modified by one of ordinary skill in the art without departing from the compositions and methods taught by the present invention.

What is claimed is:

1. A method of halting, diminishing, or inhibiting the growth of at least one of a bacterium, a fungus; a parasitic microbe, and a virus, which method comprises administering to a human being a therapeutically effective amount of at least one electron active compound that has at least two polyvalent cations, at least one of which has a first valence state and at least one of which has a second different valence state, wherein the at least one electron active compound comprises a metal oxide selected from the group consisting of Bi(III,V) oxide, Co(II,III) oxide, Cu(I,III) oxide, Mn(II,III) oxide, Pr(III,IV) oxide, $Tb_4O_7$, or a mixture thereof.

2. Tetracopper tetroxide, which comprises two copper(I) ions, two copper(III), ions and four oxygen atoms in a crystal lattice.

3. A process for preparing tetracopper tetroxide, having two copper(I) ions, two copper(III) ions, and four oxygen atoms in a crystal lattice, which process comprises:

combining a copper(I)-containing compound and a caustic solution to form a reactant solution; and heating the reactant solution to a temperature and for a time sufficient to produce a detectable amount of a tetracopper tetroxide.

4. The process of claim 3, wherein the copper(I)-containing compound comprises a non-solvated inorganic copper(I) oxide.

5. The process of claim 4, wherein non-solvated inorganic copper(I) oxide comprises cuprous oxide.

6. The process of claim 3, wherein the caustic solution comprises a strong caustic base and a peroxy acid salt.

7. The process of claim 3, wherein the strong caustic base comprises a hydroxide salt, and wherein the peroxy acid salt comprises a persulfate.

* * * * *